United States Patent [19]

Heim

[11] Patent Number: 4,806,491

[45] Date of Patent: Feb. 21, 1989

[54] METHOD AND APPARATUS FOR MEASURING THE REACTION OF AN INDICATOR TO THE PRESENCE OF VARIOUS GASES

[75] Inventor: Ulrich Heim, Reinfield, Fed. Rep. of Germany

[73] Assignee: Dragerwerk Aktiengesellschaft, Fed. Rep. of Germany

[21] Appl. No.: 936,182

[22] Filed: Dec. 1, 1986

[30] Foreign Application Priority Data

Dec. 7, 1985 [DE] Fed. Rep. of Germany ....... 3543324

[51] Int. Cl.[4] ............................................ G01N 31/22
[52] U.S. Cl. ..................................... 436/165; 422/58; 422/87
[58] Field of Search ..................... 422/58, 87; 436/165

[56] References Cited

U.S. PATENT DOCUMENTS

| | | | |
|---|---|---|---|
| 3,884,641 | 5/1975 | Kraffczyk et al. | 422/87 X |
| 4,023,930 | 5/1977 | Blunck et al. | 422/87 X |

FOREIGN PATENT DOCUMENTS

| | | |
|---|---|---|
| 2407224 | 8/1975 | Fed. Rep. of Germany . |
| 2840841 | 4/1980 | Fed. Rep. of Germany . |
| 0664091 | 5/1979 | U.S.S.R. ................................. 422/87 |

Primary Examiner—Michael S. Marcus
Assistant Examiner—Jill Johnston
Attorney, Agent, or Firm—McGlew and Tuttle

[57] ABSTRACT

A process for the measuring of flat discoloration zones of an indicator substrate, which is transported into a measuring position and treated with a gaseous test medium there, is improved with regard to the measuring dynamic and the construction of the apparatus by producing a flow of the test medium along the surface of the section of an indicator substrate held in a measuring position, by providing several optical control zones staggered in the longitudinal direction of the test flow and by connecting it with an electronic evaluation instrument for the production of the measurement in such a way that the actual measure value is formed from the measuring of the discoloration of the indicator substrate along the control zones.

3 Claims, 1 Drawing Sheet

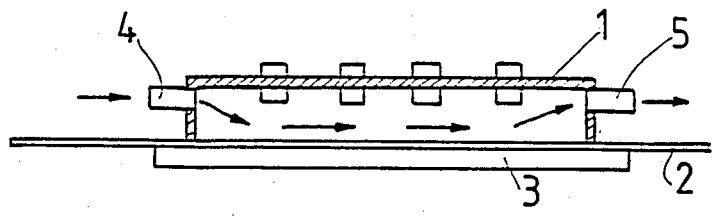
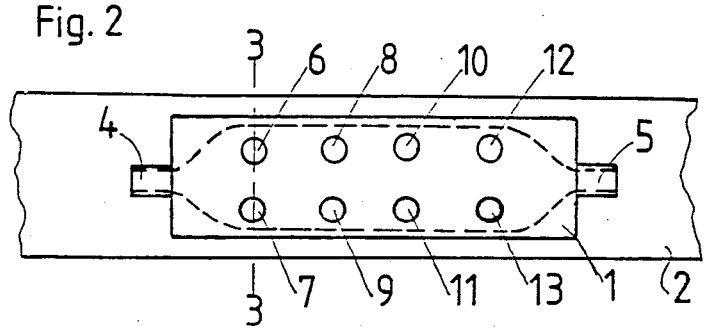
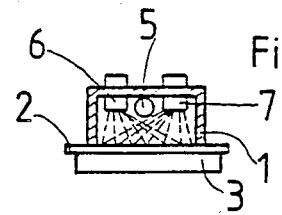
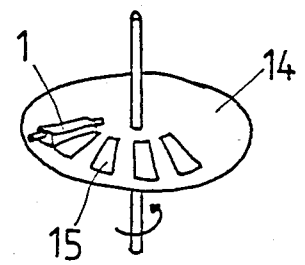
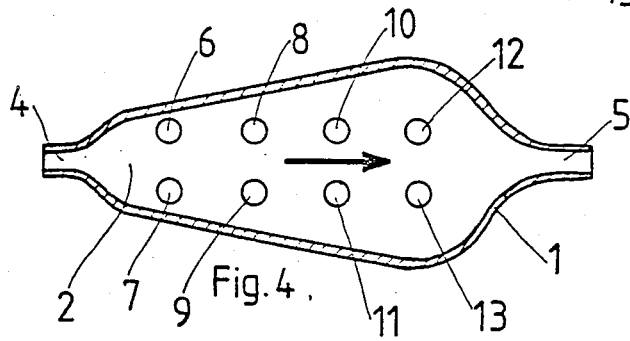

METHOD AND APPARATUS FOR MEASURING THE REACTION OF AN INDICATOR TO THE PRESENCE OF VARIOUS GASES

BACKGROUND OF THE INVENTION

Field of the Invention

This invention relates in general to gas detection devices and in particular to a new and useful method an apparatus for detecting the reaction of gases to an indicator.

The invention particular concerns a process for measuring flat discoloration zones on an indicator substrate by which a movable indicator substrate is transported into a measuring position and there treated with a gaseous medium, and the discoloration zone of the gas-treated indicator section is measured electro-optically and a measured value is determined in a measuring cycle by an electronic evaluating instrument.

A similar process is discussed in the DE-OS No. 28 04 841. There, the mean concentration of a gas or a gas component in gas mixture determined by the electro-optical measuring of the discoloration of a reagent paper band. The discoloration of the gas-treated field is determined until a predetermined threshold value is reached and the reagent paper band is then moved always by one gas-treated field, the mean concentration of the gas can be determined from the number of gas-treated fields that are discolored during the total gas-treatment time.

In another, known process according to the DE-OS No. 24 07 224, the time of the discoloration elapsed until reaching a predetermined threshold value is compared with a set retardation time. The regent paper band is moved after this time has elapsed. The mean concentration of the test gas can be determined for each time period during this time period.

A comparable state of the art is also described in the DE-Z Dragerheft 313, January to April 1979, in the report by W. Diehl, D. Gellendin, L. Grambow, K. K. Huneke and H. Zwintscher, "The Toxiwarn—a portable measuring and warning instrument for toxic gases". The construction of this instrument provides for the pressing of an indicator strip after it is rolled off a storage roll, against a gap in the outside wall of a measuring chamber, through which the gas to be tested flows. The diffuse reflection of a band section is untreated and one that is treat with gas is scanned by a system of a light source and a photo element. The concentration of the gas to be determined can be obtained from their recorded measurements. For the determination of the mean gas concentration over a time that can be selected at will, the obtained measurements are summed up and stored. The mean concentration during the measuring time period is obtained from the measurement integration and the time integration.

But the previously known processes does not meet all requirements with regard to the desired measuring dynamic and accuracy.

SUMMARY OF THE INVENTION

In accordance with the invention a better resolution power and a greater detection sensitivity are obtained by the creation of a flow of test medium along the surface of the section of indicator substrate held in the measuring position, and by providing several optical control zones, staggered in the longitudinal direction of the test flow, which are connected with the electronic evaluation instrument for producing the measurements in such a way that the actual value is formed from the measurement of the discoloration of the indicator substrate along the control zones.

The measuring dynamic, i.e. the difference between the highest and the lowest scannable measurement, is considerable increased by the provided guiding of the test medium along the sensitive layer of the indicator substrate. The length of the discoloration zone can be measured first. An integral measuring over the length of the discoloration zone can be measured first. An integral measuring over the length of the discoloration zone, taking into consideration the length of the discoloration zone as well as the degree of discoloration, may be more practical, mainly in the cases in which the transition from discolored zone to unchanged zone is gradual. This will be the case particularly when the interactions, and thus the reaction time, between the component to be determined and the reagent system does not result in a complete, quantitative conversion of the available indicator material at a given concentration.

The optical control zones can be constructed in different ways and with the use of known electro-optical building elements, according to the reflection or the transmission principle. The moveable indicator substrate, which may not only be in band form, but also in other geometrical shapes, for example a circular disc, is subdivided into test areas by the optical control zones. Each test area is optically evaluated and the well-known electronic evaluating instrument forms the sum of the products from the linearized reaction-proportional signal level of each optical control zone and from the partial areas of the gas-treated band zone. This sum of the products is a measure of the gas concentration to be determined.

In many of these type of measuring processes there exists the problem of an aging or shelf-life limitation of the indicator substrate as well as the cross sensitivity to other gases, e.g. steam. A mathematical elimination of such interferences by the electronic evaluation instrument can be obtained to advantage by performing the reflection or transmission measurement at two or more wave-lengths. Emitters of different wave-lengths can be used for this purpose at each optical control zone in connection with wide-band receivers as well as wide-band emitters with several selectively sensitive receivers.

In all of the described arrangements the recording of optical reference values of the movable indicator substrate in its initial state prior to gas treatment and the storing of these values for the later standardization of the measurements appears to be useful.

An advantageous device for performing the process can be constructed by shaping the measuring chamber in the form of a channel, locating the indicator substrate along a long area of the side wall of the measuring chamber and arranging between a gas intake and a gas outlet of the measuring chamber optical sensor elements in a longitudinal sequence so that the sensor elements have their exits connected with the electronic evaluating instrument. The construction of the optical sensor elements is determined by the type of measuring process used, i.e. transmission measurement or reflection measurement. For the reflection measurement, a row of reflection barriers, each comprising a transmitter and a receiver unit, is suitably located along the channel-shaped measuring chamber. The total volume of the measuring chamber should be small, and a flat construction with a height of approxi. 0.2 cm, a width of 0.5 cm and a length of 3 cm is to be considered suitable.

Also advantageous for the mathematical elimination of interferences is the application on the indicator substrate of various reagent systems reacting to different components of the test medium and the providing of measuring chambers in the respective positions. For example, the various reagent systems can be arranged to advantage side by side on a band-shaped indicator substrate. Another possibly advantageous approach is the applying of layers of different reagent systems to the upper and lower side of the bandshaped indicator substrate. In the former case, the measuring chambers must be arranged side by side, in the latter case, they must be arranged opposite on an upper and lower side and, if needed for reasons of construction, in the direction of the transport of the indicator substrate.

If needed, both measuring chambers are operated at different wave-lengths. Another practical example can provide the separate operation of each measuring chamber at different wave-lengths.

Depending on the intended use, the gas flow can be selected so that the test gas flows through both measuring chambers connected in series or in parallel. With the series connection, a reaction in the first measuring chamber is possible, if needed, which influences the reaction in the second measuring chamber.

An advantage may be the use of alternating reagent zones, which can be scanned one after the other with a single measuring chamber, if needed, instead of the infinite parallel arrangement of the reagent systems on the movable band shaped indicator substrate.

Instead of a band-shaped indicator substrate, a revolving indicator disc with one or several measuring chambers arranged radially on its top and/or bottom side, may also be used to advantage, if needed. Different reagent system can be used as described for the band-shaped indicator substrate.

Another practical example useful in certain cases has, at the long side wall area of the measuring chamber, a holder for depositing individual strip-like indicator chips.

The characteristics of the invention improve considerably the measuring of flat discoloration zones of an indicator substrate with regard to the measuring dynamic as well as the overall construction.

Accordingly it is the object of the invention to provide a process for measuring reaction of an indicator to various gases which comprises positioning and indicative strip and longitudinally elongated measuring chamber, directing a gas to be measured into one end of the measuring chamber and withdrawing it at the opposite end and using a plurality of indicator sensors based along the length of the chamber to electro-optically measure the reaction of the indicator to gas flow along the length of the chamber. A further object of the invention is to provide an indicating device which includes an elongated chamber which is adapted to over lie a indicative strip which has an inlet for gases at one end and then an outlet for gases at an opposite end which is provided with a plurality of indicators along the length of the strip which opto-electrically measure the reaction of the indicator strip.

A further object of the invention is to provide a measuring device for measuring reaction of gases on an indicator which is simple in design rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a longitudinal section through a measuring chamber for reflection measurements in accordance with the invention.

FIG. 2 is a top plan view of the measuring chamber according to FIG. 1;

FIG. 3 is a section through the measuring chamber shown in FIG. 2 taken along the line 3—3;

FIG. 4 a horizontal sectional view of a wedge-shaped measuring chamber;

FIG. 5 is a perspective view of a measuring chamber with revolving indicator disc.

GENERAL DESCRIPTION OF THE PREFERRED EMBODIMENTS

Referring to the drawings in particular the invention embodied therein comprises the process and apparatus for measuring the reaction of an indicator such as an indicative strip to various gases which are permitted to flow there over. In accordance with the invention as indicated in FIGS. 1 through 3 an indicative strip 2 is positioned within a measuring chamber such as a measuring chamber 1 which is longitudinally elongated an a gas can be measured as directed through a gas inlet 4 now through a gas outlet 5 and at the opposite end of measuring chamber 1. Plurality of opto-electrical indicators 6 through 13 are arranged along the length of the chamber incorporate the measure the reaction of the indicator to the flow of the gases.

In FIGS. 1 to 3 a measuring chamber 1 is show that has a low construction height of less than 1 cm for its channel-like shaped construction. Along a long side wall area of measuring chamber 1 extends a band-shaped indicator substrate or substrate indicator strip 2, which is pressed by a pressure plate 3 against an opening gap of the chamber, creating a tight seal around its edge.

A gas inlet 4 and a gas outlet 5 are provided at measuring chamber 1, through which the gaseous test medium flows parallel to the surface of band-shaped indicator substrate 2 in the direction of the arrows 20.

The four optical control zones staggered in the longitudinal direction are formed, respectively, by laterally and longitudinally spaced by reflection barriers 6,7; 8,9; 10,11; 12, 13 which comprise a transmitter unit 6, 8, 10.12 and externally arranged receiver unit 7, 9, 11, 13.

The reflection from the surface of band-shaped indicator substrate 2 is shown in FIG. 3.

An alternative arrangement of the reflection barriers 6,7; 8,9; 10,11; 12, 13 is shown in FIG. 4, which results in a decreasing sensitivity towards high measurement. This allows an expansion of the measuring range without impairing the high sensitivity for low concentrations significantly. This is obtained by the wedge-shaped formation of a measuring chamber 1, with a flow cross-section that diverges in the flow direction parallel to the surface of the indicator substrate. The spacing of the individual transmitting and receiving units arranged in rows in the direction of the flow always remains constant. As a result of this, the gaseous test medium flows across a reaction area also increasing in the direction of the flow per unit of length of the indicator substrate, i.e., also across a wedge-shaped reaction area. Instead of the wedge shape, another diverging outline may also be formed, if needed.

FIG. 5 show an indicator substrate 14 in circular disc shape, which has segment-shaped reagent systems 15. These are transported in steps under measuring chamber 1, treated with gas there, and evaluated electro-optically.

I claim:

1. A method for measuring the reaction of an indicator to various gases, comprising: positioning an indicator strip in a longitudinally elongated measuring chamber, the indicator including flat areas of discoloration reaction zones and being provided on a movable indicator substrate said step of positioning comprising transporting said substrate to a measuring position within the chamber; directing a gas to be measured into one end of the measuring chamber and withdrawing the gas at the opposite end thereof; employing a plurality of indicator sensors along the length of the chamber to electro-optically measure the reaction by the changes in color of said reaction zones of the indicator strip to the gas flow along the length of the chamber; measuring said reaction in a measuring cycle using an electronic evaluating instrument connected to the sensors, by creating a surface measuring flow of the test gas medium along the surface of a section of the indicator substrate while the indicator is held firmly in a measuring position staggering several optical control zones in a selected direction of the measuring flow; providing and connecting the zones with electronic evaluating instruments for the performance of the measurement which measures discolorations of the indicative substrate along the controlled zones; and, measuring the length of the discoloration zone.

2. A process according to claim 1 wherein the measurement is performed at least two different waves lengths.

3. A method for measuring the reaction of an indicator to various gases, comprising: positioning an indicator strip in a longitudinally elongated measuring chamber, the indicator including flat areas of discoloration reaction zones and being provided on a movable indicator substrate said step of positioning comprising transporting said substrate to a measuring position within the chamber; directing a gas to be measured into one end of the measuring chamber and withdrawing the gas at the opposite end thereof; employing a plurality of indicator sensors along the length of the chamber to electro-optically measure the reaction by the change in color of said reaction zones of the indicator strip to the gas flow along the length of the chamber; measuring said reaction in a measuring cycle using an electronic evaluating instrument connected to the sensors, by creating a surface measuring flow of the test gas medium along the surface of a section of the indicator subtrate while the indicator is held firmly in a measuring position, staggering several optical control zones in a selected direction of the measuring flow; providing and connecting the zones with electronic evaluating instruments for the performance of the measurement which measures discolorations of the indicative substrate along the controlled zones; and, performing an integral measurement over the length of the discoloration zone.

* * * * *